United States Patent
Maas et al.

(10) Patent No.: US 6,844,290 B1
(45) Date of Patent: Jan. 18, 2005

(54) OLIGOMERIZATION CATALYST

(75) Inventors: Heiko Maas, Schifferstadt (DE); Shahram Mihan, Ludwigshafen (DE); Randolf Köhn, Bath (GB); Guido Seifert, Berlin (DE); Jürgen Tropsch, Römerberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/937,815

(22) PCT Filed: Mar. 25, 2000

(86) PCT No.: PCT/EP00/02660

§ 371 (c)(1),
(2), (4) Date: Sep. 28, 2001

(87) PCT Pub. No.: WO00/58319

PCT Pub. Date: Oct. 5, 2000

Related U.S. Application Data

(63) Continuation-in-part of application No. 09/277,823, filed on Mar. 29, 1999, now abandoned.

(30) Foreign Application Priority Data

May 14, 1999 (DE) .......................... 199 22 048
Sep. 11, 1999 (DE) .......................... 199 43 544

(51) Int. Cl.$^7$ .......................... C07F 31/18; C07F 11/00
(52) U.S. Cl. .................. 502/167; 502/103; 502/123; 526/159; 526/172
(58) Field of Search ................. 502/103, 123, 502/167; 526/159, 172, 160, 165

(56) References Cited

U.S. PATENT DOCUMENTS 5,750,816 A 5/1998 Araki et al. ............... 585/512

FOREIGN PATENT DOCUMENTS

EP 780 353 6/1997

Primary Examiner—Caixia Lu
(74) Attorney, Agent, or Firm—Keil & Weinkauf

(57) ABSTRACT

An oligomerization catalyst for olefins is obtainable from a) a chromium compound $CrX_3$ and the at least equimolar amount, based on the chromium compound $CrX_3$, of a ligand L or from an existing chromium complex $CrX_3L$, in which the groups X are, independently of one another, abstractable counterions and L is a 1,3,5-triazacyclohexane of the formula I

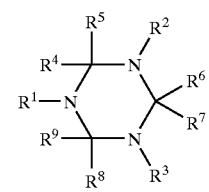

where the groups $R^1$ to $R^9$ are, independently of one another: hydrogen or organosilicon or substituted or unsubstituted carboorganic groups having from 1 to 30 carbon atoms, where two geminal or vicinal radicals $R^1$ to $R^9$ may also be joined to form a five—or six-membered ring, and b) at least one activating additive and also a process for preparing oligomers of olefins using these catalysts, the oligomers thus obtainable, and the oxo alcohols obtainable from these oligomers.

13 Claims, No Drawings

OLIGOMERIZATION CATALYST

This application is a 371 PCT/EP00/02600 filed of Mar. 25, 2000 which is a continuation in part of 09/277,823 filed Mar 29, 1999 now abandoned.

The present invention relates to an oligomerization catalyst for olefins, obtainable from a) a chromium compound $CrX_3$ and the at least equimolar amount, based on the chromium compound $CrX_3$, of a ligand L or from an existing chromium complex $CrX_3L$, in which the groups X are, independently of one another, abstractable counterions and L is a 1,3,5-triazacyclohexane of the formula I

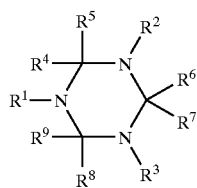

where the groups $R^1$ to $R^9$ are, independently of one another: hydrogen or organosilicon or substituted or unsubstituted carboorganic groups having from 1 to 30 carbon atoms, where two geminal or vicinal radicals $R^1$ to $R^9$ may also be joined to form a five- or six-membered ring, and b) at least one activating additive.

The present invention further relates to a process for preparing oligomers of olefins using the novel catalysts, to the oligomers obtainable in this way and to the oxo alcohols obtainable from these oligomers.

Olefin oligomers having up to 30 carbon atoms are of great economic importance. The oligomers are useful as starting materials for copolymeric plastics (e.g. 1-hexene) and as precursors of oxo alcohols (e.g. 1-hexene, the decenes and the tetradecenes). Oxo alcohols are in turn constituents of surfactants and plasticizers for plastics. In an integrated chemical production, the oligomerization processes constitute a central step in which the industrial Olefin streams which are obtained, for example, from the steam crackers are converted into products used in daily life.

The use of catalysts comprising compounds of chromium, amines and aluminum compounds in the oligomerization of a-olefins is generally known:

According to EP-A 780 353, olefins can be oligomerized, in particular trimerized, in the presence of a chromium source, a pyrrole-containing compound and a metal alkyl. However, the pretreatment of the catalyst is associated with a loss of active constituents.

DE-A 196 07 888 discloses an oligomerization catalyst for α-olefins which comprises a chromium compound and an aluminum compound together with at least one nitrogen-containing compound which may be a pyrrole. Here too, the catalyst pretreatment as described in EP-A 780 353 causes considerable losses.

EP-A 537 609 teaches a process in which ethylene is reacted in the presence of a chromium complex having a coordinated polydentate ligand and an aluminoxane to give a mixture of α-olefins having a relatively high proportion of 1-hexene. However, owing to the low catalyst activity together with a low trimerization selectivity, the economics of the process described are unsatisfactory.

It is an object of the present invention to provide stable catalysts which can be obtained more inexpensively and have improved activity and selectivity in respect of low molecular weight oligomers of olefins.

We have found that this object is achieved by the oligomerization catalysts mentioned at the outset.

We have also found a process for preparing oligomers of olefins using the novel catalysts. The invention further provides the oligomers obtainable in this way and the oxo alcohols obtainable from these oligomers.

The oligomerization catalysts of the present invention makes it possible to obtain oligomers of olefins in high yields and with a small proportion of by-products whose molar mass $M_w$ is greater than 500. In particular, the catalyst has a high selectivity in respect of the trimerization of α-olefins and especially ethene.

Triazacyclohexane and its derivatives, which differ in terms of different substitution patterns on the ring atoms, have been known for a long time and are used in a variety of ways in industry, since they can usually be prepared from readily available starting materials in a simple and inexpensive manner. Thus, triazacyclohexane derivatives are used, for example, in the desulfurization of kerosene. However, the use of triazacyclohexane and its derivatives as ligands in the preparation of organic metal complexes is not very widespread. Only a few complexes containing these ligands have been described in the literature, for example in J. Chem. Soc., Dalton Trans. (1997), 1363–1368; Z. Naturforsch., part B50 (1995), 1038–1043; Angew. Chem. Int. Ed. Engl. 33 (1994), 1877–1878; J. Organomet. Chem. 501 (1995), 303–307; Chem. Ber. 129 (1996), 25–27; J. Organomet. Chem. 520 (1996), 121–129; Inorg. Chem. 36 (1997), 6064–6069; Chem. Ber. 129 (1996), 1327–1333.

Varying the substituents on the 1,3,5-triazacyclohexane ring allows the properties of the catalyst of the present invention to be influenced. Thus, the catalyst activity can normally be increased by substituents, in particular on the nitrogen atoms. The number and geometry of the substituents additionally enables the accessibility of the central atom to the α-olefins which are to be reacted and thus also the selectivity of the reaction in respect of various starting olefins to be controlled. The chemical structure of the substituents $R^1$ to $R^9$ can therefore be varied within a wide range in order to obtain a catalyst tailored to the particular reaction.

Possible substituted or unsubstituted carboorganic groups on the 1,3,5-triazacyclohexane ring are, for example:

$C_1$–$C_{18}$-alkyl, preferably $C_1$–$C_{12}$-alkyl, e.g. methyl, ethyl, N,N-dimethylaminoethyl, n-propyl, i-propyl, butyl, pentyl, hexyl, 2-ethylhexyl, heptyl, octyl, nonyl, decyl, dodecyl, 1,1-dimethyldodecyl, 5- to 7-membered cycloalkyl which may in turn bear a $C_1$–$C_{10}$-aryl group as substituent, e.g. cyclopentyl and cyclohexyl, $C_6$–$C_{15}$-aryl such as phenyl, o-tolyl, p-tolyl, m-tolyl, 1-naphthyl and 2-naphthyl or $C_6$–$C_{15}$-arylalkyl, preferably $C_6$–$C_8$-arylalkyl such as benzyl and 1-phenylethyl.

Possible organosilicon groups are, for example: trialkylsilyl groups having from 1 to 10 carbon atoms in identical or different alkyl radicals, in particular trimethylsilyl groups.

Substituents in the C-organic groups or Si-organic groups on the 1,3,5-triazacyclohexane ring may in particular be alkyl groups with donor groups. The donor group may be neutral or anionic and may contain a heteroatom from groups 15–16 of the periodic system (according to IUPAC proposal 1985) or may be a carbanion. If it is neutral, it may be coordinately bonded to the chromium. Preferably it is coordinated to the chromium. If the donor is formally anionic, then it is covalently bonded to the metal center. The bonds may be intramolecular or intermolecular; preferably, they are intramolecular. Preference is given to neutral donors containing oxygen and/or nitrogen atoms which have free electron pairs, it also being possible for the oxygen and/or nitrogen atoms to have been inserted into an alkyl chain.

Preference is given to 1,3,5-triazacyclohexane ligands in which the groups $R^1$, $R^2$ and $R^3$ are, independently of one another, substituted or unsubstituted $C_1$–$C_{12}$-alkyl, $C_6$–$C_{15}$-aryl or $C_6$–$C_8$-arylalkyl, in particular substituted or unsubstituted $C_1$–$C_{12}$-alkyl or $C_6$-CS-arylalkyl, e.g. methyl, ethyl, N,N-dimethylaminoethyl, n-propyl, n-butyl, tert-butyl, hexyl, octyl, dodecyl, 1,1-dimethyldodecyl, 1-phenylethyl.

In the process of the present invention, particular preference is given to using 1,3,5-triazacyclohexane ligands in which the groups $R^4$, $R^5$, $R^6$, $R^7$, $R^8$ and $R^9$ are, independently of one another, hydrogen or $C_1$–$C_4$-alkyl, in particular hydrogen or methyl.

Preferred 1,3,5-triazacyclohexanes are
1,3,5-tri-tert-butyl-1,3,5-triazacyclohexane,
1,3,5-triethyl-1,3,5-triazacyclohexane,
1,3,5-tris(1-phenylethyl)-1,3,5-triazacyclohexane,
1,3,5-tris(1,1-dimethyldodecyl)-1,3,5-triazacyclohexane and
1,3-di-n-dodecyl-5-[2-(N,N-dimethylamino)ethyl]-1,3,5-triaza-cyclohexane and particularly preferably 1,3,5-tri-n-octyl-1,3,5-triazacyclohexane, 1,3,5-tri-n-dodecyl-1,3,5-triazacyclohexane,
1,3,5-tribenzyl-1,3,5-triazacyclohexane,
1,3,5-tris(2-ethylhexyl)-1,3,5-triazacyclohexane,
1,3,5-tris(2-n-propylheptyl)-1,3,5-triazacyclohexane.

The 1,3,5-triazacyclohexanes of the formula I in which the groups $R^4$ to $R^9$ are hydrogen and the groups $R^1$ to $R^3$ are identical can be prepared in a manner known per se, for example by reacting primary amines of the $R^1NH_2$ type with formaldehyde or paraformaldehyde. Correspondingly, the 1,3,5-triazacyclohexanes, which bear one methyl group and one hydrogen atom on each of the carbon atoms of the ring are obtainable via acetaldehyde.

The 1,3,5-triazacyclohexanes of the formula I in which at least one of the radicals $R^1$, $R^2$ and $R^3$ is different from the other radicals of this set can also be prepared in a manner known per se (cf., for example, Beilstein, "Handbook of Organic Chemistry", 4th Ed., Vth Suppl. Series, Springer-Verlag, Berlin, Vol. 26 (1986) 3 ff. and the references cited therein; R=octyl: J. Polym. Sci., Polym. Chem. Ed. 329 (1993), 1941–1958; J. Prakt. Chem. 327 (1985), 739–748; EP-A 620 266; DE-A 24 31 862; DE-A 41 00 856; Pharmazie 30 (1975), 699–706). A few of the known preparative methods are briefly outlined here by way of example:

1) The reaction of a mixture of two primary amines ($R^1NH_2$ and $R^2NH_2$) with formaldehyde (as aqueous solution or paraformaldehyde) leads to a mixture of various products which can be separated as follows:
   a) Distillation in the case of sufficiently small $R^1$ and $R^2$.
   b) Carrying out the reaction using a large excess of the amine $R^1NH_2$, if the symmetrical reaction product is capable of being distilled off. After the distillation, the unsymmetrical product then remains.
   c) Selective crystallization of one product.
   d) Complexation of the mixture of the 1,3,5-triazacyclohexanes with the chromium compound, for instance $CrCl_3$, and separation of the chromium complexes obtained, for instance by column chromatography.

2) Reaction of an amine $R^1NH_2$ with an excess of formaldehyde to give a mixture of symmetrically substituted 1,3,5-triazacyclohexane and the corresponding 1-oxa-3,5-diazacyclohexane: in a second step, the 1-oxa-3,5-diazacyclohexane is reacted with an amine $R^2NH_2$ (if desired in the presence of an acid catalyst), resulting in the ring oxygen being replaced by an $R^2N$.

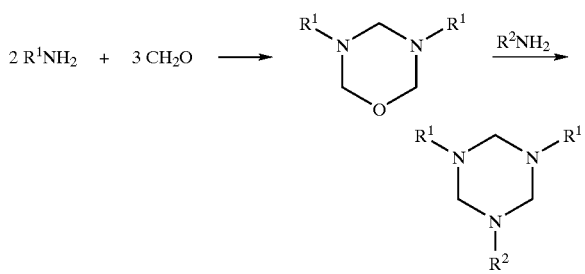

The product mixture can be separated as described under 1).

3) Reaction of a symmetrical 1,3,5-triazacyclohexane having a small $R^1$ (methyl or ethyl) at about 130° C. with an amine $R^2NH_2$. At this temperature, $R^1NH_2$ is given off and a mixture of unsymmetrical 1,3,5-triazacyclohexanes is formed.

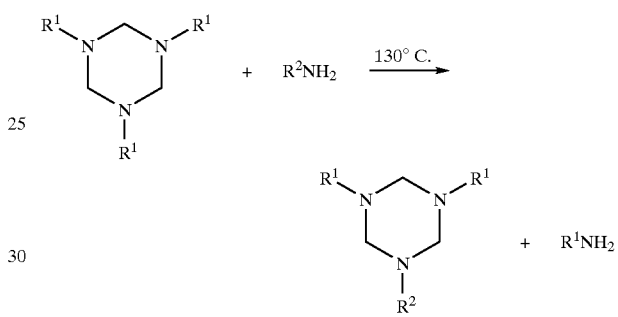

The separation can be carried out as described under 1).

4) Reaction of two different symmetrical 1,3,5-triazacyclohexanes with one another, resulting in substituent exchange. The products can be separated as described under 1).

Suitable groups X in the chromium compounds $CrX_3$ or the chromium complexes $CrX_3L$ are any abstractable counterions that are suitable for this purpose in organometallic chemistry, in particular halogen such as fluorine, bromine, iodine and especially chlorine, tosylate, triflate, tetrafluoroborate, hexafluorophosphate, hexafluoroantimonate, tetraphenylborate, $C_1$- to $C_{10}$-carboxy, especially 2-ethylhexanoate, alkyl groups, for example methyl, ethyl, i-propyl, phenyl benzyl, bulky noncoordinating anions such as $B(C_6F_5)_4$—.

The groups X are selected in particular such that the chromium compounds $CrX_3$ or chromium complexes $CrX_3L$ in which they are present possess good solubility in the particular solvent used.

As starting materials for the chromium compounds $CrX_3$ and the chromium complexes $CrX_3L$, use is made of, for instance, chromium halides such as $CrCl_3$, $CrBr_3$, $Cr(triflate)_3$, $Cr(III)$ alkoxylates such as the 2-ethylhexanoate and also complexes of these chromium compounds with weakly bound, neutral complexing ligands which may be displaced by the 1,3,5-triazacyclohexane and possibly by the five-membered aromatic N-heterocycle, e.g. ether complexes such as $CrCl_3(tetrahydrofuran)_3$, $CrCl_3(dioxane)_3$, ester complexes such as $CrCl_3(n$-butyl acetate), $CrCl_3(ethyl\ acetate)$, alcohol complexes such as $CrCl_3(i$-propanol)$_3$, $CrCl_3(2$-ethylhexanol)$_3$, amine complexes such as $CrCl_3(pyridine)_3$, $CrCl_3(i$-propylamine)$_2$, or nitrile complexes such as $CrCl_3(acetonitrile)_3$.acetonitrile.

In a preferred embodiment of the process of the present invention, use is made of oligomerization catalysts which have been prepared using chromium complexes $CrX_3L$ which have been prepared and isolated beforehand in-house.

The chromium complexes $CrX_3L$ are moreover obtainable by methods known to those skilled in the art or by methods analogous to these (cf., for example, W. A. Herrmann, A. Salzer: "Synthetic Methods of Organometallic and Inorganic Chemistry", Vol. 1—Literature, Laboratory Techniques, and Common Starting Materials, Thieme Verlag, Stuttgart, 1996).

The preparation of the chromium complexes $CrX_3L$ in situ is generally carried out by dissolving or suspending the chromium compound $CrX_3$ in the reaction medium and adding the 1,3,5-triazacyclohexane either as such or in dissolved form.

In the oligomerization process of the present invention, preference is given to using chromium complexes $CrX_3L$ in which X and L have the following meanings:

X are, independently of one another: halogen, tosylate, triflate, alkyl,

L is a 1,3,5-triazacyclohexane of the formula 1, in which the groups $R^4, R^5, R^6, R^7, R^8$ and $R^9$ are, independently of one another, hydrogen or $C_1$–$C_4$-alkyl, in particular hydrogen or methyl, and in which $R^1, R^2$ and $R^3$ are, independently of one another, methyl, ethyl, N,N-dimethylaminoethyl, propyl, n-butyl, tert-butyl, hexyl, octyl, dodecyl, 1,1-dimethyldodecyl or (1-phenyl) ethyl.

Particular preference is given to using chromium complexes $CrX_3L$, in which X and L have the following meanings:

X are, independently of one another: chlorine., tosylate,

L is a 1,3,5-triazacyclohexane of the formula I, in which the groups $R^4, R^5, R^6, R^7, R^8$ and $R^9$ are, independently of one another, hydrogen or methyl and in which $R^1, R^2$ and $R^3$ are, independently of one another, methyl, ethyl, N,N-dimethylaminoethyl, propyl, n-butyl, tert-butyl, hexyl, octyl, dodecyl, 1,1-dimethyldodecyl or 1-phenylethyl.

In one preferred embodiment of the process of the invention, the activating additive is composed of an unsubstituted or substituted five-membered aromatic N-heterocycle and at least one aluminum alkyl, some of whose alkyl groups may have been replaced by halogen and/or alkoxy.

Suitable five-membered aromatic N-heterocycles are ones having 1, 2, 3 or 4, preferably 1 or 2, nitrogen atoms in a five-membered aromatic ring. The five-membered aromatic N-heterocycles may be substituted on the ring carbons by groups which are inert under the reaction conditions, e.g. alkyl groups, preferably methyl and/or ethyl, or two adjacent carbon atoms of the five-membered aromatic N-heterocycle may together be part of a fused-on aromatic carbocyclic system which may in turn bear inert groups. Examples of such N-heterocycles are unsubstituted and substituted pyrroles, pyrazoles, imidazoles, triazoles and tetrazoles, e.g. pyrrole, 2,5-dimethylpyrrole, indole, carbazole, pyrazole, indazole, imidazole, benzimidazole. Preference is given to using pyrroles and, in particular, alkyl-substituted pyrroles, especially 2,5-dimethylpyrrole.

As aluminum alkyl, in which some of the alkyl groups may be replaced by halogen and/or alkoxy, it is possible to use aluminum alkyls of the formulae $AlR_3$, $AlR_2Hal$, $AlRHal_2$, $AlR_2OR'$, $AlRHalOR'$ and $Al_2R_3Hal_3$ and mixtures thereof, where R and R' are each, independently of one another, methyl, ethyl or a straight-chain or branched $C_3$–$C_8$-alkyl group and Hal is fluorine, bromine, iodine or especially chlorine, for example trimethylaluminum, triethylaluminum, tri-n-propylaluminum, tri-iso-propylaluminum, tributylaluminum, diethylaluminum chloride, diethylaluminum bromide, diethylaluminum ethoxide, diethylaluminum phenoxide, ethylaluminum ethoxide chloride. Preference is given to using aluminum alkyls of the $AlR_3$ and $AlRHal_2$ type, with triethylaluminum or a mixture of triethylaluminum and ethylaluminum dichloride being particularly preferred.

As an alternative to aluminum alkyls in which some of the alkyl groups are replaced by halogen and/or alkoxy, it is also possible to use mixtures of the corresponding aluminum alkyls and suitable cocatalysts, from which the desired mixed aluminum compounds are formed in situ in the reactor.

Suitable cocatalysts are alkyl halides, alkylsilicon halides and Lewis-acid metal halides, preferably n-butyl chloride, n-butyl iodide, trimethylsilyl chloride, trimethylsilyl bromide, tin tetrachloride, germanium chloride and especially n-butyl bromide.

In the system comprising aluminum alkyl, some of whose alkyl groups may be replaced by halogen and/or alkoxy, and cocatalyst, the two components are present in a molar ratio of from 1:3 to 30:1, preferably from 1:1 to 15:1.

In the process of the present invention, the amount of chromium compound $CrX_3$ or chromium complex $CrX_3L$ is normally in the range from $1\times10^{-7}$ to 1 mol, preferably from $1\times10^{-6}$ to 0.1 mol and in particular from $1\times10^{-5}$ to 0.01 mol per kg of reaction mixture.

The amount of five-membered aromatic N-heterocycle is normally in the range from $1\times10^{-8}$ to 100 mol, preferably from $1\times10^{-7}$ to 1 mol and in particular from $1\times10^{-5}$ to 0.05 mol per kg of reaction mixture.

The amount of aluminum alkyl in which some of the alkyl groups may be replaced by halogen and/or alkoxy is normally in the range from $1\times10^{-8}$ to 500 mol, preferably from $1\times10^{-7}$ to 10 mol and in particular from $5\times10^{-5}$ to 0.5 mol, per kg of reaction mixture.

In the process of the present invention, the molar ratio of the components (a), (b) and (c) is 1:0.1–100:0.1–500, preferably 1:0.1–10:1–100 and in particular 1:1–5:5–50.

Very particular preference is given to a catalyst consisting of (a) (1,3,5-tri-n-octyl-1,3,5-triazacyclohexane)$CrCl_3$ or (1,3,5-tribenzyl-1,3,5-triazacyclohexane)$CrCl_3$, (b) 2,5-dimethylpyrrole and (c) triethylaluminum and ethylaluminum dichloride, where these components are present in a molar ratio of 1:0.1–10:0.1–100, preferably 1:1–5:5–50. The molar ratio of triethylaluminum and ethylaluminum dichloride in component (c) is 1–50:1, preferably 3–20:1.

The oligomerization is preferably carried out in a solvent. Solvents which can be used for the oligomerization are straight-chain, branched or alicyclic saturated hydrocarbons having from 1 to 20 carbon atoms, e.g. butane, pentane, 3-methylpentane, hexane, heptane, 2-methylhexane, octane, cyclohexane, methylcyclohexane, 2,2,4-trimethylpentane, or decalin, straight-chain or branched halogenated hydrocarbons such as dichloroethane, aromatic hydrocarbons such as benzene, toluene, xylene, ethylbenzene, mesitylene, or tetralin and the oligomeric reaction products which are liquid under the reaction conditions, e.g. 1-hexene itself. The solvents can be used either individually or as mixtures.

Preferred oligomerization catalysts in accordance with the invention are also those comprising an alkylalumoxane as the activating additive.

In this context, very particular preference is given to those ligands L in which the groups $R^1$, $R^2$ and $R^3$ in part or in whole, and independently of one another, are a group which carries a substituent attached via a carbon atom, in particular an alkyl, aryl or silyl group, in the P position or in a position even more remote from the nitrogen atom of the 1,3,5-triazacyclohexane ring. With particular preference, this substituent is in the β position. With further particular preference, this substituent is a β-alkyl substituted alkyl, especially 2-ethylhexyl or 2-n-propylheptyl. Among these ligands L, very particular preference in turn is given to those in which the groups $R^4$, $R^5$, $R^6$, $R^7$, $R^8$ and $R^9$ are hydrogen.

Suitable alkylalumoxanes are known, for example, from DE-A 30 07 725, their structures being largely unelucidated. They are products of the careful partial hydrolysis of aluminum alkyls (cf. DE-A 30 07 725). These products are evidently not present in their pure form but are instead mixtures of open-chain and cyclic structures of type IIa and IIb which are presumably in dynamic equilibrium with one another.

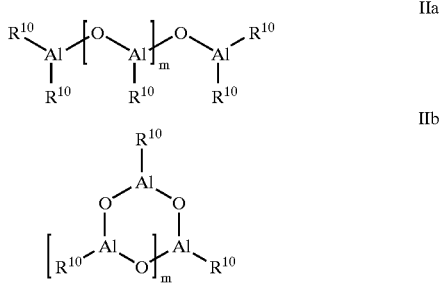

In the formulae IIa and IIb, the groups $R^{10}$ are identical or different and independently of one another are $C_1$–$C_{12}$-alkyl such as methyl, ethyl, n-propyl, i-propyl, n-butyl, i-butyl, sec-butyl, tert-butyl, n-pentyl, i-pentyl, sec-pentyl, neopentyl, 1,2-dimethylpropyl, i-amyl, n-hexyl, i-hexyl, sec-hexyl, n-heptyl, i-heptyl, noctyl, n-nonyl, n-decyl, and n-dodecyl; 4D preferably $C_1$–$C_6$-alkyl such as methyl, ethyl, n-propyl, i-propyl, n-butyl, i-butyl, sec-butyl, tert-butyl, n-pentyl, i-pentyl, sec-pentyl, neopentyl, 1,2-dimethylpropyl, i-amyl, n-hexyl, i-hexyl, sec-hexyl, with methyl being particularly preferred. m is an integer from 0 to 40, preferably from 0 to 25, and with particular preference from 0 to 22.

In the literature, cagelike structures for alumoxanes are also discussed (cf. Organometallics 1996, 15, pages 2213–26; Macromol. Symp. 1995, 97, pages 15–25).

The alkylalumoxanes are effective as activating additives in the context of the present invention independently of their structural constitution.

The amount of the activating alkylalumoxane used is dependent on its nature. The ratio of chromium compound $CrX_3$ and/or chromium complex $CrX_3L$ to the activating alkylalumoxane is generally from 1:0.1 to 1:10 000, preferably from 1:1 to 1:1 000.

Suitable solvents when using an oligomerization catalyst comprising $CrX_3$, a ligand L and the alkylalumoxane, or comprising $CrX_3L$ and the alkylalumoxane, are aprotic solvents, examples being the aliphatic or aromatic hydrocarbons cited earlier above as solvents, and especially toluene.

In another preferred embodiment of the process of the invention, an oligomerization catalyst is used which comprises as activating additive at least one boron compound and at least one aluminum alkyl, some of whose alkyl groups may have been replaced by halogen and/or alkoxy.

Examples of suitable boron compounds are those containing electron-withdrawing radicals (e.g. trispentafluorophenylborane, N,N-dimethylanilinium tetrakispentafluorophenylborate, tri-n-butylammonium tetrakispentafluorophenylborate, N,N-dimethylanilinium tetrakis(3,5-bisperfluoromethyl)-phenylborate, tri-n-butylammonium tetrakis(3,5-bisperfluoromethyl) phenylborate, and tritylium tetrakispentafluorophenylborate). These activating additives are known from EP-A 468 537 and also EP-A 426 638.

Preference is given to tritylium tetrakispentafluorophenylborate, trispentafluorophenylborane, and especially dimethylanilinium tetrakis(pentafluorophenyl)borate.

The amount of the activating boron compound used is dependent on its nature. The ratio of chromium compound $CrX_3$ and/or chromium complex $CrX_3L$ to the activating boron compound is generally from 1:0.1 to 1:10 000, preferably from 1:1 to 1:1 000.

Suitable aluminum alkyls some of whose alkyl groups may be replaced by halogen and/or alkoxy are the representatives of this class of substance cited on earlier on above, in the amounts specified there relative to the chromium compound $CrX_3$ and/or the chromium complex $CrX_3L$.

Suitable solvent in this context are aprotic solvents, examples being the aliphatic or aromatic hydrocarbons cited earlier on above as solvents, and especially toluene.

Preferred olefins for oligomerization by the process of the invention are straight-chain and branched α-olefins having preferably from 2 to 10, in particular from 2 to 6 and especially from 2 to 4, carbon atoms and mixtures thereof, and with very particular preference, in each case on its own: 1-propene, 1-butene, 1-hexene, 1-decene, and especially ethene, 1-butene, especially 1-butene in the mixture with its isomers such as is present, for instance, in the raffinate II.

Owing to the tendency of the aluminum compounds in particular and possibly the cocatalysts to hydrolyze, the oligomerization is generally to be carried out with very substantial exclusion of moisture. Techniques known per se can be employed for this purpose. The oligomerization is preferably carried out under protective gas using baked-out apparatuses. Protective gases which can be used are all gases which are chemically inert under the reaction conditions, advantageously nitrogen or argon. In addition, the α-olefin to be reacted can itself assume the function of a protective gas as long as it has a sufficiently high vapor pressure under the reaction conditions.

The oligomerization is preferably carried out at from 1 to 120° C., in particular from 70 to 110° C., and preferably at a pressure in the range from 3 to 120 bar. The pressure is advantageously selected so that the reaction mixture is liquid at the temperature set.

The process of the present invention can be carried out batchwise or continuously, with the continuous mode being preferred on an industrial scale.

Reactors suitable for carrying out the process of the present invention continuously are well known to those skilled in the art, for example from Ullmann's Enzyklopädie der technischen Chemie, Volume 1, 3rd edition, 1951, page 743 ff.; pressure-rated reactors are also described there on page 769 ff.

The remaining boundary conditions of such oligomerization reactions are set by a person skilled in the art on the basis of his general technical knowledge, which he can, for example, derive from DE-A 196 07 889.

The deactivation of the catalyst at the end of the reaction can be carried out using, in principle, a number of substances which all have the ability to hydrolyze aluminum alkyl compounds, for example water and monoalcohols having from 1 to 10 carbon atoms. Mineral acids may also be added to these substances.

The products of the oligomerization of the present invention are advantageously purified by distillation. In this way, for example, the reaction product from the ethene oligomerization can be fractionated to give not only the main (hexene) fraction consisting predominantly of 1-hexene but also a decene fraction and a tetradecene fraction. The latter two fractions consist predominantly of branched, internal olefins.

To achieve a high total conversion in the process of the present invention, unreacted starting material can be recovered and returned to the reaction.

Preferred products of the process of the present invention are trimers of α-olefins, especially of α-olefins having from 2 to 6 carbon atoms, and particularly preferably the 1-hexene obtainable from ethene.

The oligomers obtainable with the process of the invention are especially suitable for preparing monoalcohols for plasticizers and surfactants. For this purpose the oligomers are appropriately subjected to hydroformylation, in the course of which mixtures of the aldehydes and alcohols, chain-extended by one carbon atom, are formed, these mixtures being subsequently hydrogenated to give the desired alcohols. The implementation of the hydroformylation and hydrogenation is known per se to the skilled worker and therefore requires no further elucidation (cf., e.g., Beller et al., Journal of Molecular Catalysis A 104 (1995) pages 17–85). The following examples illustrate the invention.

EXAMPLES

A) Catalysts 2,5-Dimethylpyrrol, $CrCl_3(THF)_3$, 1,3,5-tribenzyl-1,3,5-triazacyclohexane and triethylaluminum were procured from Aldrich Chemical Company Ltd. and kieselguhr from Riedel de Haen AG.

Preparation of the 1,3,5-triazacyclohexanes

Preparation of 1,3,5-tri-n-octyl-1,3,5-triazacyclohexane 100 g (0.774 mol) of n-octylamine were added in small portions to a suspension of 20.2 g (0.673 mol) of paraformaldehyde in 500 ml of toluene which was cooled to 0° C. On subsequent heating of the mixture to the boiling point, the paraformaldehyde went into solution. Water and toluene were then distilled off. The residue was freed of volatile constituents at 1 mbar, taken up in 100 ml of methanol and filtered through a 1 cm thick layer of silica gel. The volatile constituents of the filtrate were subsequently removed at 1 mbar, giving 62.3 g (83% yield) of the title compound as a viscous, clear liquid. The following 1,3,5-triazacyclohexanes were prepared in an analogous manner:

1,3,5-tri-n-dodecyl-1,3,5-triazacyclohexane
1,3,5-tri-tert-butyl-1,3,5-triazacyclohexane
1,3,5-triethyl-1,3,5-triazacyclohexane
1,3,5-tris(1-phenylethyl)-1,3,5-triazacyclohexane
1,3,5-tris(1,1-dimethyldodecyl)-1,3,5-triazacyclohexane
1,3-di-n-dodecyl-5-[2-(N,N-dimethylamino)ethyl]-1,3,5-triaza-cyclohexane
1,3,5-tris(2-ethylhexyl)-1,3,5-triazacyclohexane
1,3,5-tris(2-n-propylheptyl)-1,3,5-triazacyclohexane Preparation of the catalysts Preparation of "chromium complex 1": [(1,3,5-tri-n-octyl-1,3,5-triazacyclohexane)$CrCl_3$]

662 mg (1.768 mmol) of the tetrahydrofuran complex $CrCl_3(THF)_3$ and 728 mg (1.855 mmol) of 1,3,5-tri-n-octyl-1,3,5-triazacyclohexane (see above) were placed in a reaction flask at 25° C. At −78° C., 100 ml of diethyl ether which had been dried over sodium were condensed into this mixture. The suspension obtained in this way was stirred for about 30 minutes at 25° C. It was then filtered through a frit and the filter residue was washed with diethyl ether until the washings were no longer green. The residue was then dried at 25° C. and 1 mbar, giving 885 mg of the title compound (98% yield).

Preparation of "chromium complex 2": [1(1,3,5-tribenzyl-1,3,5-triazacyclohexane)$CrCl_3$]

10 ml of dry diethyl ether were placed under argon in a baked-out glass apparatus at 25° C. 749 mg (20 mmol) of the tetrahydrofuran complex $CrCl_3(THF)_3$ were suspended therein, and a solution of 715 mg (20 mmol) of 1,3,5-tribenzyl-1,3,5-triazacyclohexane in 2 ml of diethyl ether were added dropwise to the mixture while stirring. The mixture was subsequently stirred for another 30 minutes at 20° C. and then filtered under argon through a frit. The filter residue was washed three times with 10 ml each time of diethyl ether and then dried at 25° C. and 1 mbar. This gave 0.64 g of the title compound as a violet solid.

Preparation of the "chromium complexes 3–10"

Using a method analogous to the preparation of the complexes 1 and 2, the following complexes of chromium (III) chloride were prepared:

"chromium complex 3": [(1,3,5-tri-n-dodecyl-1,3,5-triazacyclohexane)$CrCl_3$]
"chromium complex 4": [(1,3,5-tri-tert-butyl-1,3,5-triazacyclohexane)$CrCl_3$]
"chromium complex 5": [(1,3,5-triethyl-1,3,5-triazacyclohexane)$CrCl_3$]
"chromium complex 6": [(1,3,5-tris(1-phenylethyl)-1,3,5-triazacyclohexane)$CrCl_3$]
"chromium complex $7$": [(1,3,5-tris(1,1-dimethyldodecyl)-1,3,5-triazacyclohexane)$CrCl_3$]
"chromium complex 8": [(1,3-di-n-dodecyl-5-[2-(N,N-dimethylamino)ethyl]-1,3,5-triaza-cyclohexane)$CrCl_3$]
"chromium complex 9": [(1,3,5-tris(2-ethylhexyl)-1,3,5-triazacyclohexane)$CrCl_3$]
"chromium complex 10": [(1,3,5-tris(2-n-propylheptyl)-1,3,5-triazacyclohexane)$CrCl_3$]

B) Oligomerizations

Example 1

Oligomerization of Ethene in the Presence of "Complex 1" and 2,5-Dimethylpyrrole A steel autoclave having a capacity of 100 ml was baked out at 105° C. in a stream of argon for 60 minutes. 14.5 mg of "chromium complex 1" were subsequently introduced at 25° C., followed by 25 ml of n-heptane which had been dried over sodium and 0.5 ml of a _solution of 143 mg of 2,5-dimethylpyrrole in 10 ml of n-heptane, corresponding to 0.075 mmol of 0,2,5-dimethylpyrrole. The autoclave was subsequently flushed three times with ethene at atmospheric pressure. 0.75 ml of a 1 molar solution of triethylaluminum in n-heptane was then added, followed by pressurization with 25 bar of ethene. The temperature was subsequently increased to 80° C. and the ethene pressure was increased to 40 bar. The contents of the autoclave were stirred for 2 hours under these conditions, after which the autoclave was cooled and vented. The catalyst was deactivated by addition of 1 ml of water to the reaction mixture. The constituents insoluble in the reaction mixture were separated off, dried and weighed. The productivity was 18.6 kg per 1 g of chromium in the catalyst. The relative amounts of the products obtained were determined by gas chromatography using n-heptane as internal standard:

| | |
|---|---|
| hexenes | 44.4% by weight |
| decenes | 33.1% by weight |
| tetradecenes | 10.9% by weight |
| "polymers" | 1.5% by weight |

Examples 2 to 11

Examples 2 to 11 were carried out using a method analogous to Example 1. n-Butyl bromide (n-BuBr) and ethylaluminum dichloride (EADC) were used as 0.1M solutions in n-heptane. The starting materials, the associated amounts and the results of the experiments are shown in Table 1 below.

TABLE 1

Data on Examples 2 to 11

| Ex. | Chromium complex CrX$_3$L | Cat [μmol] | DMP [μmol] | TEA [μmol] | Cocat [μmol] | n-Heptane [ml] | C6 [% by weight] | C10 [% by weight] | C14 [% by weight] | Polym [% by weight] | Productivity [kg/g Cr] |
|---|---|---|---|---|---|---|---|---|---|---|---|
| 2 | 2 | 25 | 75 | 750 | — | 25 | 56.1 | 27.5 | 6.5 | 7.3 | 27.4 |
| 3 | 2 | 10 | 30 | 300 | — | 10 | 62.1 | 21.7 | 4.7 | 7.6 | 44.8 |
| 4 | 3 | 10 | 30 | 300 | — | 10 | 53.5 | 25.0 | 6.3 | 9.1 | 33.5 |
| 5 | 4 | 10 | 30 | 300 | — | 10 | 59.4 | 24.4 | 7.3 | 2.6 | 21.1 |
| 6 | 5 | 10 | 30 | 300 | — | 10 | 63.3 | 21.1 | 5.3 | 8.8 | 16.4 |
| 7 | 6 | 10 | 30 | 300 | — | 10 | 55.6 | 23.9 | 7.0 | 4.4 | 19.3 |
| 8 | 7 | 10 | 30 | 300 | — | 10 | 61.7 | 23.5 | 6.0 | 4.9 | 28.0 |
| 9 | 8 | 10 | 30 | 300 | — | 10 | 48.3 | 23.0 | 7.0 | 10.5 | 24.8 |
| 10 | 2 | 10 | 30 | 300 | n-BuBr 30 | 10 | 68.1 | 20.7 | 6.2 | 2.2 | 75.3 |
| 11 | 2 | 10 | 30 | 300 | EADC 30 | 10 | 82.8 | 14.3 | 2.1 | 0.3 | 106.1 |

Abbreviations:
Cat Amount of chromium complex CrX$_3$L
DMP Amount of 2,5-dimethylpyrrole
TEA Amount of triethylaluminum
Cocat Cocatalyst and amount
n-Heptan Amount of n-heptane
C6 Proportion of hexenes in the product
C10 Proportion of decenes in the product
C14 Proportion of tetradecenes in the product
Polym Proportion of polymers in the product Example 12

Trimerization of 1-Butene in the Presence of "Chromium Complex 9" and Methylaluminoxane and Hydroformylation of the Resulting Trimer to the Corresponding Oxo Alkohol a) Trimerization A steel autoclave of a volume of 2500 ml was baked out at 120° C. under a stream of argon. At 25° C., 750 mg of "chromium complex 9", and 500 g of toluene, dried over sodium, were charged to the autoclave which was then flushed three times with 1-butene. Thereafter, 50 g of a 1 M solution of methylalumoxane in toluene and, via an airlock, 500 g of 1-butene were introduced into the autoclave. The temperature in the autoclave was then raised to 40° C. and the pressure was adjusted to 15 bar using nitrogen gas. After two hours of reaction under the conditions thus established, the autoclave was cooled and let down. The catalyst was deactivated by adding 2-propanol. Subsequent analysis by gas chromatography of the reactor discharge (800 g) found the only oligomers present to be isomeric dodecenes. The dodecane mixture obtained by hydrogenation had an ISO index of 2.3.

b1) Hydroformylation in the presence of cobalt carbonyl 1.06 kg of the dodecene mixture prepared in accordance with section a) were hydroformylated with 4.0 g of Co$_2$(CO)$_8$ at 185° C. and 280 bar of CO/H$_2$ (1:1) with the addition of 100 g of water in a 2500 ml rotary stirred autoclave in 5 hours. The reaction discharge was subsequently decobalted oxidatively at 90° C. using 10% strength acetic acid and with introduction of air. The oxo product thus obtained is hydrogenated over a fixed-bed Co/Mo catalyst in a 2500 ml tube reactor operated in downflow mode at 175° C. and 280 bar of H$_2$ with the addition of 10% by weight of water, based on the organic phase. The alcohol mixture produced in this reaction was worked up by distillation and the tridecanol mixture thus isolated had an OH number of 279 mg KOH/g. A mean degree of branching of 2.7 was found by $^1$H-NMR spectroscopy.

b2) Hydroformylation with rhodium biscarbonyl acetylacetonate/polyethyleneimine 50 mg of rhodium biscarbonyl acetylacetonate, 4.5 g of a polyethyleneimine of molecular mass M$_w$=460000, in which 60% of all the nitrogen atoms had been amidated using lauric acid, 800 g of the dodecene mixture prepared in accordance with section a) and 196 g of toluene were heated to 150° C. in a 2500 ml stirred lift autoclave under CO/H$_2$ (1:1). A pressure of 280 bar was set by means of CO/H$_2$. After 7 hours, the autoclave was cooled, let down and emptied. An olefin conversion of 93% was found by gas chromatography. The oxo product thus obtained was hydrogenated in a 2500 ml tube reactor operated in downflow mode over a fixed-bed Co/Mo catalyst at 175° C. and 280 bar of H$_2$ with the addition of 10% by weight of water, based on the organic phase. The alcohol mixture produced in this reaction was worked up by distillation and the resulting tridecanol mixture had an OH number of 279 mg KOH/g. A mean degree of branching of 2.9 was measured by $^1$H-NMR spectroscopy.

Examples 13–22

Trimerization in the Presence of "Chromium Complex 9" and Methylaluminoxane a) Alternative preparation of "chromium complex 9"

15 ml of (+/−)-2-ethylhexylamine (92 mmol) were dissolved in 200 ml toluene, and 2.75 g of paraformaldehyde (92 mmol) were added. After the mixture had been stirred for one hour, the toluene/water azeotrope was distilled off until a boiling-point of 110° C. had been reached. The mixture was then cooled in a stream of argon to below the boiling point, and 4.82 g of anhydrous CrCl$_3$ (31 mmol) were added. After again distilling off a few ml of toluene and cooling under the stream of argon, 0.5 g zinc powder is added. On further distillative removal of toluene, the suspension turned into a deep violet solution. Toluene was distilled off for 30 minutes more and the residue was cooled to 25° C. After the zinc powder had settled out, the deep violet solution was decanted off in air and the solvent was removed on a rotary evaporator. The violet, somewhat oily solid residue was dissolved in acetone and the solution was filtered. The resulting deep violet solution was admixed with water until the solution above the violet precipitate had only a slight violet coloration. After filtration, the violet residue was dried for 40 hours under reduced pressure (approximately 1 Pa) at 50° C. toward the end. 13.12 g (74%) of the violet "chromium complex 9" were obtained.

b) Implementation of the trimerizations

The trimerizations were conducted in a 1 l four-necked flask equipped with contact thermometer, stirrer, heating mantle and gas inlet tube, into which from 30 to 50 μmol of "chromium complex 9", in 250 ml of toluene were introduced under argon at 40° C.

Methylalumoxane ("MAO") was used in the form of a 1.6 M solution in toluene.

The boron compound used was dimethylanilinium tetrakis(pentaflourophenyl)borate ("DMAB"). Following its addition, the reaction mixture was heated to 70° C., then cooled to 40° C. and admixed with triisobutylaluminum ("TIBAL").

From 20 to 40 l/h of ethene or 1-butene were passed through the pale green/yellow solution obtained following the addition of MAO or DMAB/TIBAL, or the corresponding amount of 1-hexene was added dropwise.

In the course of the experiment, the temperature was held constant at temperature T for the reaction time t. The reaction was ended by adding 15 ml of concentrated hydrochloric acid in 50 ml of methanol and the reaction mixture was subsequently stirred for 15 min. Then 250 ml of methanol were added and stirring was continued for 15 mins more. Following filtration to remove any insoluble polymer forms, the product was washed three times with water and dried over sodium sulfate. Yield and product distribution were determined by gas chromatography from the solution thus obtained. Further reactant data and the results of the experiments are given in Table 2.

Examples 23 to 26

Trimerization in the Presence of "Chromium Complex 10" and Methylalumoxane a) Alternative preparation of "chromium complex 10"

The preparation took place in analogy to the alternative preparation of chromium complex 9 in accordance with Examples 13–22.

b) Implementation of the trimerizations

The trimerizations of Examples 23–25 were carried out in analogy to Examples 13–22 in toluene as the solvent.

The reaction of Example 26, on the other hand, took place in a 1000 ml autoclave under a pressure of 40 bar, again in toluene.

The further reactant data and the results of the experiments are given in Table 3.

TABLE 2

Data for Examples 13–22

| Ex. | Amount of chromium complex 9 [mg] | (μmol) | Atom ratio Al:Cr | Atom ratio B[1]:Cr | T [° C.] | Monomer | DMP[3] [μmol] | t [min] |
|---|---|---|---|---|---|---|---|---|
| 13 | 16.6 | 33.6 | 300:1 | — | 40 | $C_2H_4$ + 5 ml 1-hexene | — | 60 |
| 14 | 19.0 | 32.6 | 350:1 | — | 40 | $C_2H_4$[4] | — | 60 |
| 15 | 30.2 | 51.9 | 50: | 2.2:1 | 40 | $C_2H_4$[4] | — | 60 |
| 16 | 25.5 | 43.8 | 350:1 | — | 40 | $C_2H_4$[4] | — | 60 |
| 17 | 23.8 | 40.9 | 50:1[2] | 2:1 | 40 | 500 ml 1-hexene | 123 | 90 |
| 18 | 20.4 | 35.1 | 50:1 | 2:1 | 40 | 500 ml 1-hexene | 60 | — |
| 19 | 21.2 | 36.4 | 300:1 | — | 40 | 500 ml 1-hexene | — | 60 |
| 20 | 26.6 | 45.7 | 350:1 | — | 40 | 1-butene[4] | — | 60 |
| 21 | 22.2 | 38.1 | 50:1 | 10:1 | 40 | 1-butene[4] | — | 60 |
| 22 | 18.4 | 31.6 | 300:1 | — | 20 | 1-butene[4] | — | 60 |

| | Polymer | Products [g] | | | | Activity of the catalyst used [kg/(mol Cr*h)] | | | | |
|---|---|---|---|---|---|---|---|---|---|---|
| Ex. | [g] | $C_6$ | $C_{10}$ | $C_{14}$ | $C_{18}$ | Polymer | $C_6$ | $C_{10}$ | $C_{14}$ | $C_{18}$ | Total |
| 13 | — | 13.0 | 16.5 | 3.08 | — | — | 387 | 488 | 91 | — | 965 |
| 14 | 0.52 | 6.9 | 10 | 2.3 | — | 16 | 213 | 307 | 71 | — | 607 |
| 15 | 0.9 | 4.9 | 7.78 | 2.5 | — | 17 | 94 | 149 | 48 | — | 308 |
| 16 | 0.56 | 5.96 | 12.5 | 2.99 | — | 12.8 | 136 | 286 | 68 | — | 502 |
| 17 | — | — | — | — | 3.47 | — | — | — | — | 84 | 84 |
| 18 | — | — | — | — | 1.02 | — | — | — | — | 29.1 | 29.1 |
| 19 | — | — | — | — | 2.7 | — | — | — | — | 75.8 | 75.8 |
| 20 | — | | 2.08 | | — | — | | 43.1 | | — | 43.1 |
| 21 | — | | 2.58 | | | — | | 67 | | | 67 |
| 22 | — | | 1.19 | | | — | | 37.65 | | | 37.65 |

[1] Activation is by addition of DMAB and TIBAL
[2] Triethylaluminum was used instead of TIBAL
[3] 2,5-Dimethylpyrrole
[4] Gas was passed through

TABLE 3

Data for Examples 23–26

| Ex. | Amount of chromium complex 10 [mg] | (μmol) | Atom ratio Al:Cr | Atom ratio B[1]:Cr | T [° C.] | Monomer | DMP[3] [μmol] | t [min] |
|---|---|---|---|---|---|---|---|---|
| 23 | 19.5 | 29.3 | 300:1 | — | 40 | $C_2H_4$[4] | — | 60 |
| 24 | 28.3 | 42.5 | 50:1[5] | 5.3:1 | 40 | 1-butene[4] | 127.5 | 60 |
| 25 | 12.1 | 18.2 | 500:1 | — | 50 | ethene | — | 30 |
| 26 | 55 | 83 | 300:1 | — | 40 | 200 ml 1-butene | — | 60 |

| Ex. | Polymer [g] | Product [g] | | | | Activity of the catalyst used [kg/(mol Cr*h)] | | | | |
|---|---|---|---|---|---|---|---|---|---|---|
| | | $C_6$ | $C_{10}$ | $C_{14}$ | $C_{18}$ | Polymer | $C_6$ | $C_{10}$ | $C_{14}$ | $C_{18}$ | Total |
| 23 | 0.43 | 9.02 | 10.9 | 2.06 | 0.16 | 14.7 | 308 | 372 | 70 | 5.5 | 770 |
| 24 | — | $C_{12}$: 2.31 | | | | — | $C_{12}$: 54.3 | | | | 54.3 |
| 25 | 0.07 | 6.63 | 1.96 | — | — | 3.8 | 730 | 215 | 0 | 0 | 945 |
| 26 | — | $C_{10}$: 0.24, $C_{12}$: 2.09 | | | | — | $C_{10}$: 2.9, $C_{12}$: 25.2 | | | | 28.1 |

[1])Activation takes place by addition of DMAB and TIBAL
[2])Triethylaluminum was used instead of TIBAL
[3])2,5-Dimethylpyrrole
[4])Gas was passed through
[5])Use of triethylaluminum

We claim:

1. A catalyst obtained from
   a) a chromium compound $CrX_3$ and the at least equimolar amount, based on the chromium compound $CrX_3$, of a ligand L or from an existing chromium complex $CrX_3L$, in which the groups X are, independently of one another, abstractable counterions and L is a 1,3,5-triazacyclohexane of the formula I

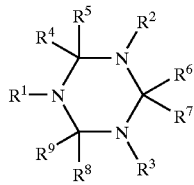

I where the groups $R^1$ to $R^9$ are, independently of one another: hydrogen or organosilicon or substituted or unsubstituted carboorganic groups having from 1 to 30 carbon atoms, where two geminal or vicinal radicals $R^1$ to $R^9$ may also be joined to form a five- or six-membered ring, and b) at least one activating additive selected from the group consisting of (i) and (ii) wherein:
   i) is a combination of an unsubstituted or substituted five-membered aromatic N-heterocycle and at least one aluminum alkyl, wherein some of the alkyl groups of the aluminum alkyl are optionally replaced by halogen and/or alkoxy, and
   ii) is an alkylalumoxane.

2. The catalyst defined in claim 1, wherein the groups $R^1$, $R^2$ and $R^3$ in the 1,3,5-triazacyclohexane I are, independently of one another, substituted or unsubstituted $C_1$–$C_{12}$-alkyl, $C_6$–$C_{15}$-aryl or $C_7$–$C_9$-arylalkyl.

3. The catalyst defined in claim 1, wherein the groups $R^1$, $R^2$ and $R^3$ in the 1,3,5-triazacyclohexane I are, independently of one another, substituted or unsubstituted $C_1$–$C_{12}$-alkyl or $C_7$–$C_8$-arylalkyl.

4. [(1,3,5-Tris(2-n-propylheptyl)-1,3,5-triazacyclohexane) $CrCl_3$].

5. [(1,3,5-Tris(2-ethylhexyl)-1,3,5-triazacyclohexane) $CrCl_3$].

6. A process for preparing oligomers having up to 30 carbon atoms by reaction of an olefin or a mixture of olefins at from 0 to 150° C. and pressures of from 1 to 200 bar in the presence of the catalyst defined in claim 1.

7. The catalyst defined in claim 1, wherein the groups $R^4$, $R^5$, $R^6$, $R^7$, $R^8$ and $R^9$ in the 1,3,5-triazacyclohexane I are, independently of one another, hydrogen or methyl.

8. A process as claimed in claim 6, wherein the olefin or mixture of olefins is selected from straight-chain and branched α-olefins having from 2 to 4 carbon atoms.

9. A process as claimed in claim 6, wherein the olefin or mixture of olefins is selected from 1-butene and 1-butene in mixture with its isomers.

10. A process as claimed in claim 6, wherein the olefin or mixture of olefins is employed in form of a raffinate comprising 1-butene in mixture with its isomers.

11. A process as claimed in claim 6, wherein the olefin is ethene.

12. A process as claimed in claim 6, wherein the catalyst is obtained from
   a) a chromium compound $CrX_3$ and the at least equimolar amount, based on the chromium compound $CrX_3$, of a ligand L or from an existing chromium complex $CrX_3L$, in which the groups X are, independently of one another, abstractable counterions and L is a 1,3,5-triazacyclohexane of the formula I

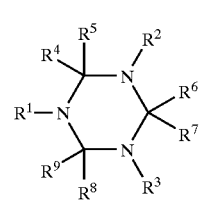

I where the groups $R^1$ to $R^9$ are, independently of one another:

hydrogen or organosilicon or substituted or unsubstituted carboorganic groups having from 1 to 30 carbon atoms, where two geminal or vicinal radicals $R^1$ to $R^9$ may also be joined to form a five- or six-membered ring, and $R^1$, $R^2$ and $R^3$ in part or in whole, and independently of one another, are a group which carries a substituent attached via a carbon atom, in the p position relative to the nitrogen atom of the 1,3,5-triazacyclohexane ring, and b) the alkylalumoxane.

13. A process as claimed in claim 12, wherein the olefin is ethene.

* * * * *

UNITED STATES PATENT AND TRADEMARK OFFICE
CERTIFICATE OF CORRECTION

PATENT NO. : 6,844,290 B1  
APPLICATION NO. : 09/937815  
DATED : January 18, 2005  
INVENTOR(S) : Maas et al.

Page 1 of 1

It is certified that error appears in the above-identified patent and that said Letters Patent is hereby corrected as shown below:

Title page,  
Item [63], Related U.S. Application Data, delete "Continuation-in-part of Application No. 09/277,823, filed on Mar. 29, 1999, now abandoned" and replace with the following paragraph:  
-- The patent claims priority of U.S. application Serial No. 09/277,823, filed March 29, 1999, in accordance with PCT Article 8 and 35 U.S.C. § 119(a) and (b). --.

Column 15,  
Line 63, "$C_7$–$C_g$–arylalkyl" should read -- $C_7$–$C_8$–arylalkyl --.

Column 18,  
Line 1, "p position" should read -- β position --.

Signed and Sealed this

Twenty-seventh Day of June, 2006

JON W. DUDAS  
*Director of the United States Patent and Trademark Office*